(12) United States Patent
Wang-Lee

(10) Patent No.: US 7,882,575 B2
(45) Date of Patent: *Feb. 8, 2011

(54) PROTECTIVE GOGGLE ASSEMBLY

(75) Inventor: Tzu-Feng Wang-Lee, Taizi Village Jende Hsiang (TW)

(73) Assignee: Jiann Lih Optical Co., Ltd., Taizi Village Jende Hsiang (TW)

( * ) Notice: Subject to any disclaimer, the term of this patent is extended or adjusted under 35 U.S.C. 154(b) by 542 days.

This patent is subject to a terminal disclaimer.

(21) Appl. No.: 11/964,853

(22) Filed: Dec. 27, 2007

(65) Prior Publication Data

US 2008/0301858 A1 Dec. 11, 2008

Related U.S. Application Data

(63) Continuation-in-part of application No. 11/758,891, filed on Jun. 6, 2007, now Pat. No. 7,725,959.

(51) Int. Cl.
*A61F 9/02* (2006.01)
(52) U.S. Cl. .............................. 2/431; 2/452
(58) Field of Classification Search ..................... 2/431, 2/442, 452

See application file for complete search history.

(56) References Cited

U.S. PATENT DOCUMENTS

| 4,977,627 | A  | * | 12/1990 | Metcalfe et al. | 2/437 |
| 5,617,588 | A  | * | 4/1997 | Canavan et al. | 2/428 |
| 7,322,051 | B1 | * | 1/2008 | Wang et al. | 2/448 |
| 7,343,631 | B2 | * | 3/2008 | Lin | 2/448 |
| 7,604,346 | B2 | * | 10/2009 | Wang | 351/43 |
| 7,725,959 | B2 | * | 6/2010 | Wang-Lee | 2/428 |

* cited by examiner

*Primary Examiner*—Katherine Moran
(74) *Attorney, Agent, or Firm*—Alan Kamrath; Kamrath & Associates PA

(57) ABSTRACT

A protective goggle assembly has a goggle frame having a rigid goggle body formed on a front side. The goggle body has recesses formed on two sides of a lower end so that a resilient face engaging portion is integrally formed with a rear side of the goggle frame. The resilient face engaging portion includes edges on two sides of a lower end, which edges are formed with a curved shape based on a human face contour. When the goggle frame and the lens are assembled with a strap buckled to the two sides for use and with the resilient face engaging portion on the rear side of the goggle frame in contact with a user's face and cheekbones, the recesses formed on the two sides of the lower end of the rigid goggle body provide the resilient face engaging portion with a larger space for flexible adjustment.

2 Claims, 4 Drawing Sheets

PROTECTIVE GOGGLE ASSEMBLY

CROSS REFERENCE

This application is a continuation-in-part application of U.S. application Ser. No. 11/758,891 filed on Jun. 6, 2007, now U.S. Pat. No. 7,725,959.

BACKGROUND OF THE INVENTION

1. Technical Field

The present invention relates to a protective goggle assembly and, more particularly, to a protective goggle assembly in which a goggle frame is combined with a resilient face engaging portion to provide a comfortable fit when the goggle assembly is worn by users having different facial shapes and higher cheekbones. The goggle frame, a lens and a strap can be assembled in a simple and convenient way so as to be stably positioned, and the assembly can be quickly disassembled when not in use.

2. Description of Related Art

The goggle industry has developed protective goggle assemblies of various configurations. A protective goggle assembly generally comprises: an integrally formed goggle frame; a lens shaped corresponding to the goggle frame and installed on a front side thereof; and a strap attached to two sides of the goggle frame and the lens for comfortably fitting on a wearer's head. Thus, a protective goggle assembly is formed that can be worn for both safety and comfort. An example of such protective goggle assembly is disclosed in U.S. Pat. No. 5,617,588 published on Apr. 8, 1997 with the title of "Snap Together Protective Goggle Construction with Toric Lens", in which a protective goggle assembly has a rigid goggle body 12 integrally formed with a resilient face engaging portion 18 located adjacent thereto. A tab 73 and a detent 56 are provided at an upper end and a lower end of a middle section of the goggle body 12, respectively, and cooperate with a slot 74 and a notch 58 disposed at corresponding locations on an integrally formed lens 14. In addition, side walls 42 extending from two sides of the lens 14 are correspondingly inserted into slots formed on two outer sides of the goggle body 12 (as shown in FIG. 8). Moreover, a strap receiving member 78 is formed on each of two sides of the goggle body 12 for securing and receiving a strap 80 therethrough. When the protective goggle assembly 10 is worn by a user, the resilient face engaging portion 18 provided on an inner side of the goggle body 12 is in contact with the user's face and cheekbones, with the strap 80 fitting on the user's head. While such protective goggle assembly serves the intended protective function, it is not comfortable to the face when worn by someone having a wider face or higher cheekbones as the resilient face engaging portion 18 is excessively pressed towards the rigid goggle body 12. Furthermore, disassembling of the strap is an inconvenient operation. When a user tries to remove the strap 80, he or she must push a flap of the strap receiving member 78 outwards and then pull out the strap 80 that passes through the flap.

SUMMARY OF THE INVENTION

In view of the problems associated with the use of existing protective goggle assemblies, the present invention provides an improved protective goggle assembly in which a goggle frame with a resilient face engaging portion combined therewith can provide a comfortable fit when worn by users having different facial shapes and higher cheekbones. The goggle frame, a lens and a strap can be assembled in a simple and convenient way so as to be stably positioned, and the assembly can be quickly disassembled when not in use.

A primary objective of the present invention is to provide a protective goggle assembly having a goggle frame with a lens installed therein. A rigid goggle body is integrally formed on a front side of the goggle frame. The goggle body is formed with recesses on two sides of a lower end thereof, so that a resilient face engaging portion is integrally formed with a rear side of the goggle frame. The resilient face engaging portion includes edges located on two sides of a lower end thereof which edges are formed with a curved shape based on a human face contour. Therefore, when the goggle frame and the lens are assembled with a strap buckled to the two sides thereof for use and with the resilient face engaging portion on the rear side of the goggle frame in contact with the face and cheekbones of a user, the recesses formed on the two sides of the lower end of the rigid goggle body provide the resilient face engaging portion with a larger space for flexible adjustment. Thus, a comfortable fit is offered for users having different facial shapes or higher cheekbones.

A second objective of the present invention is to provide a protective goggle assembly in which a rigid goggle body provided on a front side of a goggle frame has: an engaging portion located at a middle section of an upper side of the goggle body and includes a groove opening outwards; and a concave section located at a middle section of a lower side of the goggle body and provided with a vertical through hole located adjacent to the concave section. An integrally formed lens has a connecting portion located at a middle section of an upper side of the lens and fitting into the groove of the goggle body. A downwardly extending protrusion, located at a middle section of a lower side of the lens, can be inserted into the vertical through hole on the goggle body. In addition, the goggle body further includes a designed through hole on each of two sides thereof, with raised portions protruding outwards from a periphery of the designed through hole. A tenon is located on a side of each of the designed through holes. The lens further includes a designed through hole on each of two sides thereof corresponding to the respective designed through holes on the goggle body. An aperture is located on a side of each of the designed through holes on the lens for receiving the corresponding tenon. A strap is combined with a buckle at each of two ends thereof. Each of the buckles has an engaging section extending from a side thereof. The engaging section forms a boundary portion at an end thereof for sequentially penetrating the respective designed through holes of the lens and the goggle body. When the two buckles are rotated, the boundary portions of the respective engaging sections press stably against an inner surface of the two designed through holes of the goggle body. Therefore, the goggle frame, the lens and the strap can be assembled in a simple and convenient way so as to be stably positioned, and the assembly can be quickly disassembled when not in use.

A third objective of the present invention is to provide a protective goggle assembly in which a resilient face engaging portion integrally formed with and located adjacent to a side of a rigid goggle body of a goggle frame includes a plurality of air vents on two sides of a lower end of the face engaging portion. Thus, the protective goggle assembly allows good ventilation when in use.

DETAILED DESCRIPTION OF THE PREFERRED EMBODIMENT

Figure 2:
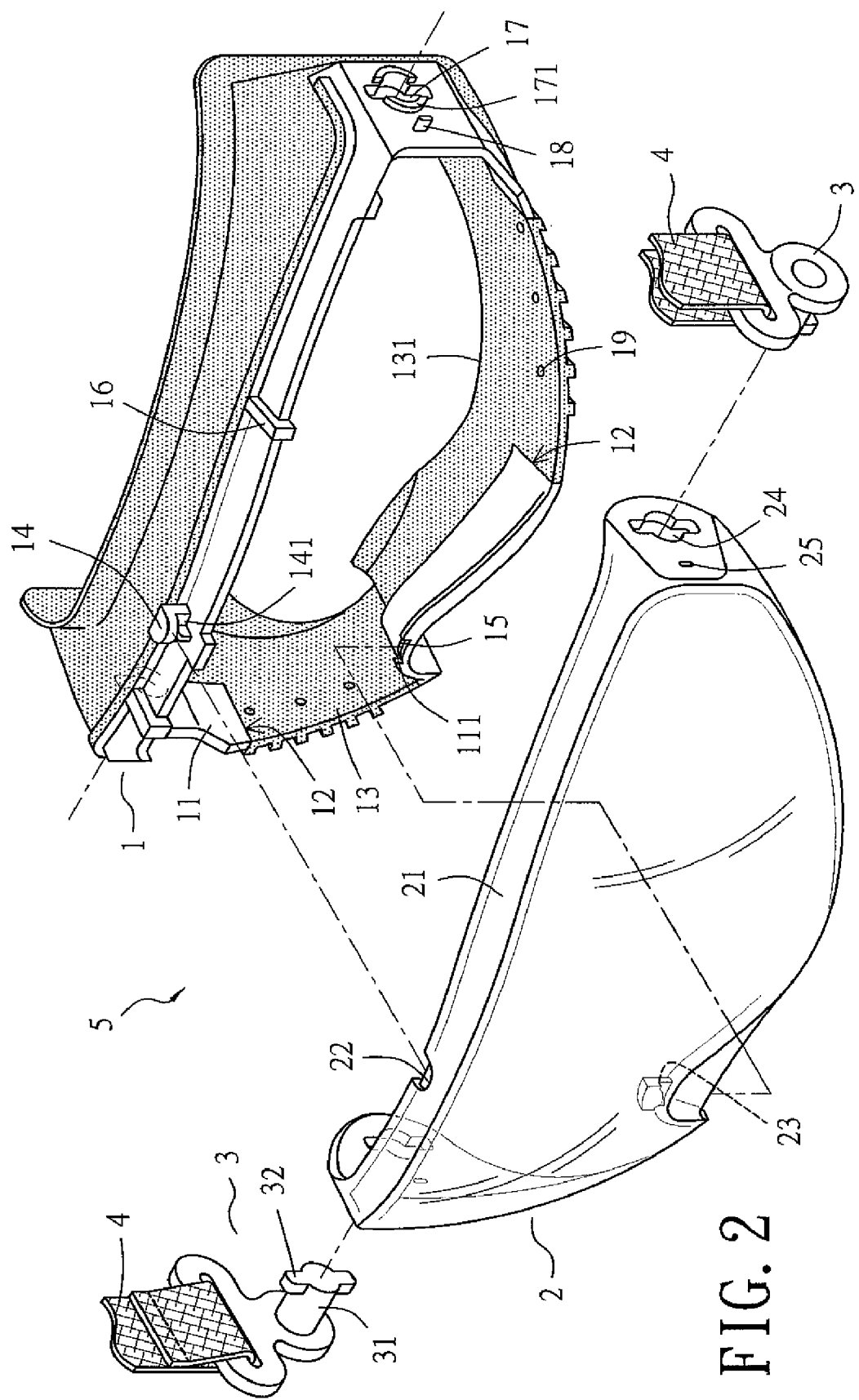
FIG. 2 is a perspective exploded view of the protective goggle assembly according to the present invention showing components thereof.

Referring to FIG. 2, a protective goggle assembly 5 of the present invention comprises an integrally formed goggle frame 1, a lens 2 and a strap 4 having its respective ends attached to respective buckles 3.

The goggle frame 1 has an integrally formed, rigid goggle body 11 located on a front side thereof. The goggle body 11 has recesses 12 on two sides of a lower end thereof. A resilient face engaging portion 13 is integrally formed with a rear side of the goggle body 11. The resilient face engaging portion 13 includes edges 131 on two sides of a lower end thereof (also referring to FIG. 5), which edges 131 are formed with a curved shape based on a human face contour. The rigid goggle body 11 has an engaging portion 14 located at a middle section of an upper side of the goggle body 11 and including a groove 141 opening outwards. The rigid goggle body 11 further has concave section 111 located at a middle section of a lower side of the goggle body 11 and provided with a vertical through hole 15 located adjacent to a side of the concave section 111. The rigid goggle body 11 further includes more than one rib 16 disposed along an upper periphery thereof. The rigid goggle body 11 also includes a designed through hole 17 on each of two sides of the goggle body 11 with raised portions 171 protruding outwards from a periphery of the designed through hole 17. A tenon 18 is located on a side of each designed through hole 17. In addition, the resilient face engaging portion 13 located adjacent to a side of the goggle body 11 includes a plurality of air vents 19 on two sides of a lower end of the face engaging portion 13.

The lens 2 is a rigid lens shaped according to the goggle frame 1 and has a covering edge 21 extending backwards from a periphery of the lens 2. The lens 2 further includes a connecting portion 22 located at a middle section of an upper side thereof and a protrusion 23 located at the middle section of a lower side thereof. In addition, the lens 2 has a designed through hole 24 on each of two sides thereof and an aperture 25 located on a side of each designed through hole 24.

Each end of the strap 4 (referring to FIGS. 1 and 2) is attached to a buckle 3. Each of the buckles 3 has an engaging section 31 extending from a side thereof. The engaging section 31 forms a boundary portion 32 at an end thereof.

Figure 1:
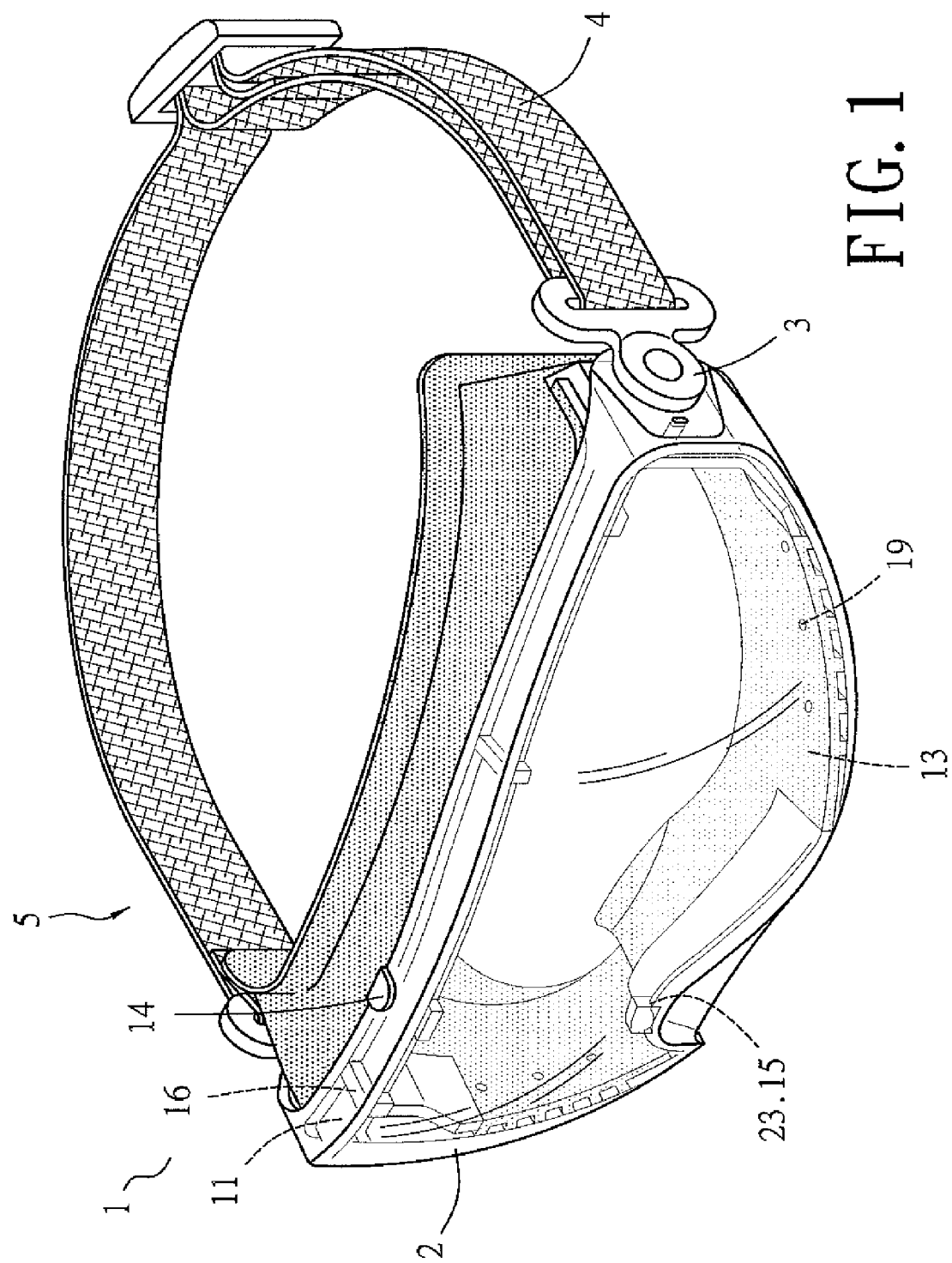
FIG. 1 is a perspective view showing an appearance of a protective goggle assembly according to the present invention.
Figure 3:
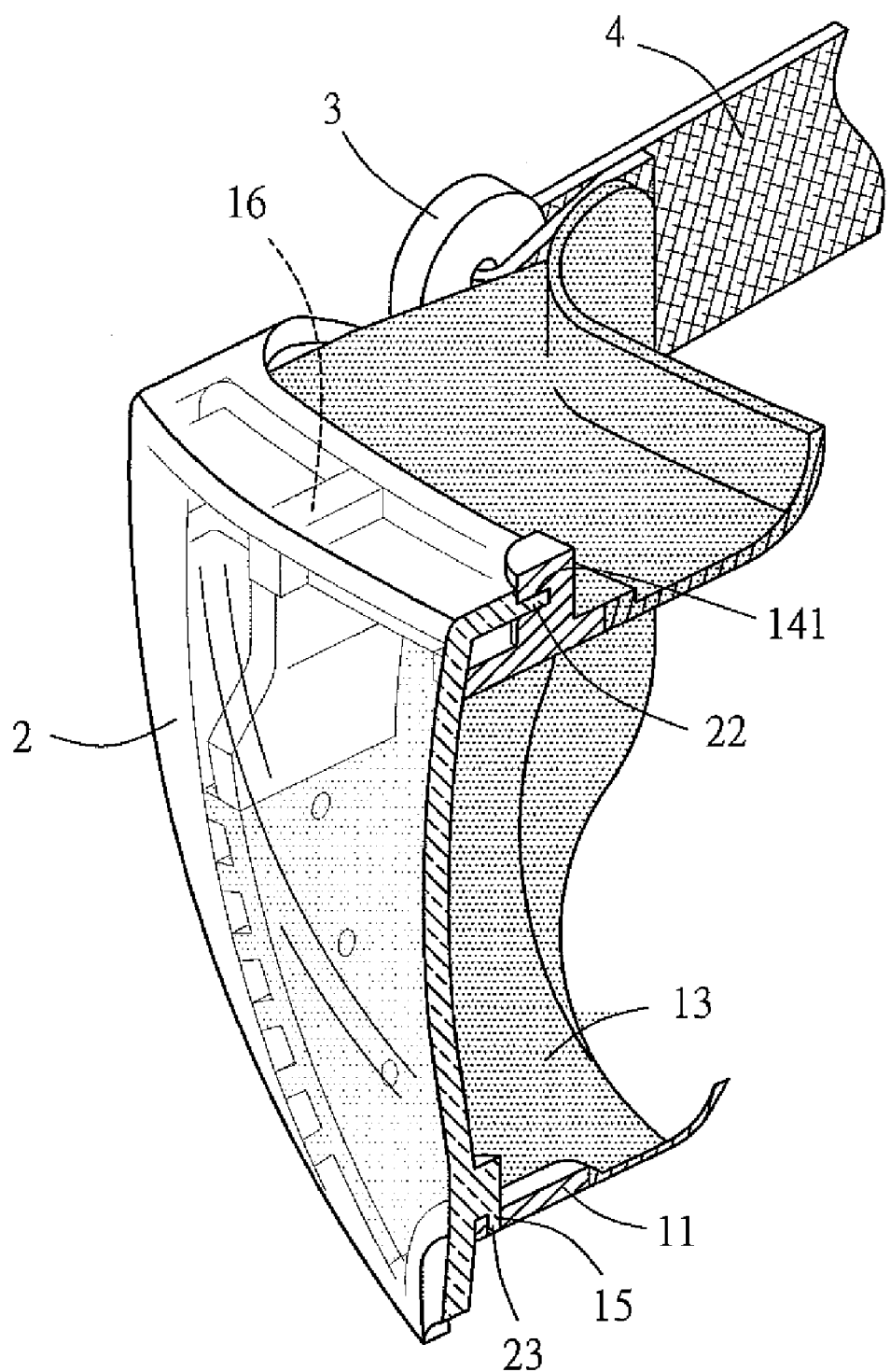
FIG. 3 is a schematic cross-sectional view of the protective goggle assembly according to the present invention showing the assembly of a goggle frame and a lens.
Figure 4:
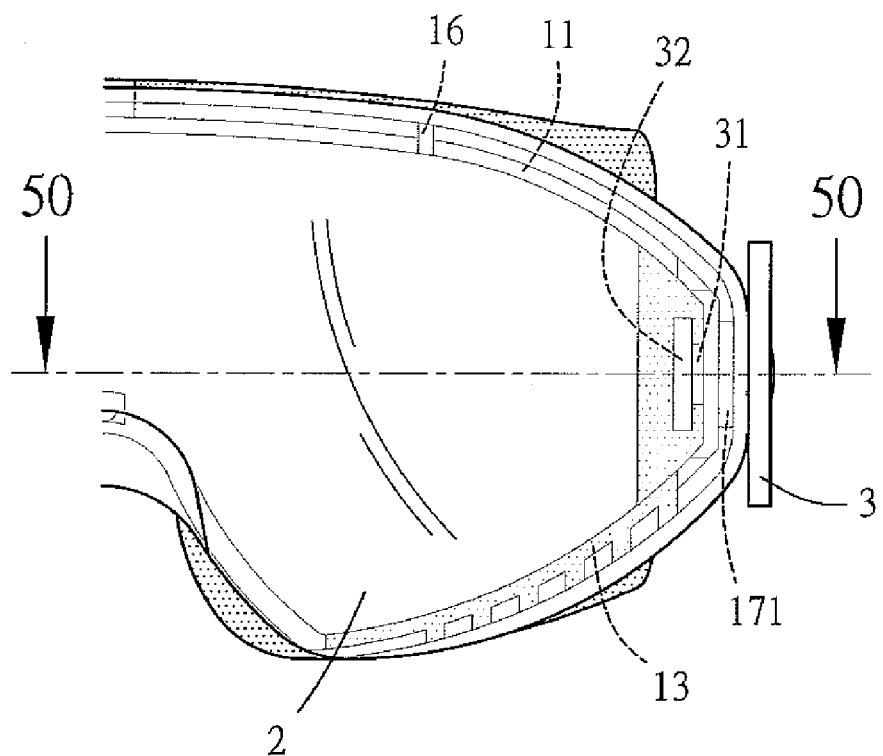
FIG. 4 is a front view of the protective goggle assembly according to the present invention showing assembly of the goggle frame, the lens and buckles of a strap.
Figure 5:
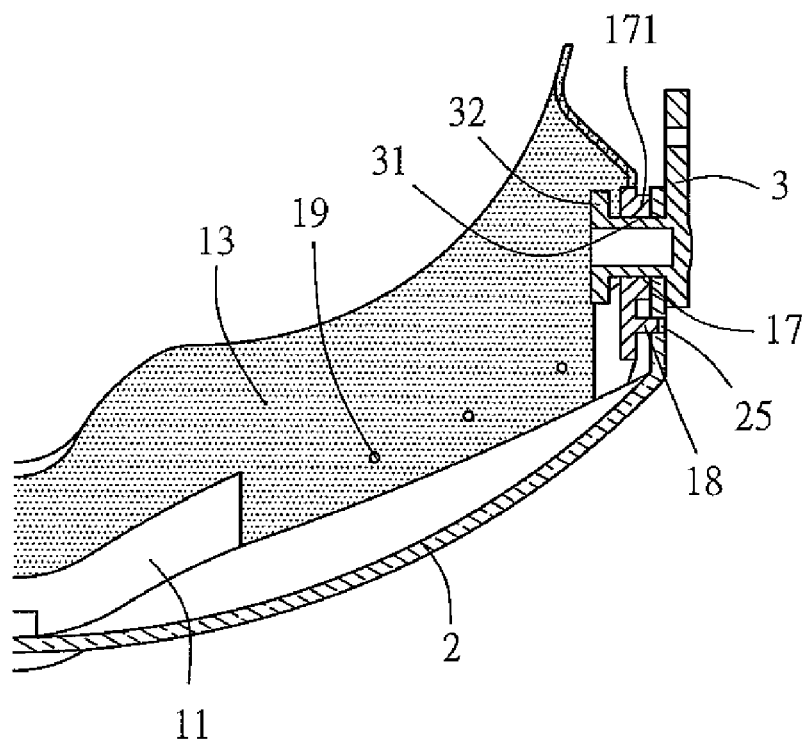
FIG. 5 is a cross-sectional view taken along line 50-50 in FIG. 4.

Referring to FIG. 3, when the integrally formed goggle frame 1, the lens 2, and the strap 4 with the buckles 3 at both ends thereof are to be assembled, the front end of the goggle frame 1 is fitted into the covering edge 21 formed at the periphery of the lens 2. Next, the connecting portion 22 at the middle section of the upper side of the lens 2 is inserted into the groove 141 of the goggle body 11; the downwardly extending protrusion 23 at the middle section of the lower side of the lens 2 is fitted into the vertical through hole 15 of the goggle body 11 (referring also to FIG. 1); and an inner surface of the covering edge 21 of the lens 2 is stably supported by the ribs 16 on the upper periphery of the goggle body 11, as shown in FIG. 3. Then, the designed through holes 17 on the two sides of the goggle body 11 are aligned with the designed through holes 24 on the lens 2 as shown in FIGS. 4 and 5, so that the raised portions 171 protruding from the periphery of the designed through holes 17 of the goggle body 11 press against the inner surface of the lens 2 and so that the tenons 18 on both sides of the goggle body 11 pass through the corresponding apertures 25 on the lens 2. Finally, the boundary portions 32 formed at the ends of the engaging sections 31 located on one side of the buckles 3 which are combined with the two ends of the strap 4 penetrate sequentially the respective designed through holes 24, 17 of the lens 2 and the goggle body 11. When the two buckles 3 are rotated (by 90° as illustrated herein), the boundary portions 32 formed at the ends of the respective engaging sections 31 press stably against an inner surface of the two designed through holes 17 of the goggle body 11, as shown in FIG. 5. Thus, the integrally formed goggle frame 1, the lens 2 and the strap 4 with the buckles 3 at both ends thereof are assembled for use in a simple and convenient way to form a protective goggle assembly 5 whose components are stably restrained in position, as shown in FIG. 1.

The protective goggle assembly assembled in the above-mentioned way has the following advantages when in use:

1. When the goggle frame and the lens are assembled with the strap buckled to the two sides thereof for use and with the resilient face engaging portion on the rear side of the goggle frame in contact with the face and cheekbones of a user, the recesses formed on the two sides of the lower end of the rigid goggle body provide the resilient face engaging portion with a larger space for flexible adjustment. Thus, a comfortable fit is offered for users having different facial shapes or higher cheekbones.

2. The buckles on the strap are buckled to the two sides of the lens and the goggle body by directly putting the engaging sections at ends of the buckles sequentially into the corresponding designed through holes on the lens and the goggle body and then rotating the buckles, so that the boundary portions of the engaging sections firmly press against the inner surface of the goggle body. Thus, the positions of the goggle frame, the lens and the strap are easily and conveniently restrained. When the assembly needs to be disassembled, it can also be done rapidly.

3. A front side of the goggle frame can be esthetically enhanced by providing the rigid goggle body and the resilient face engaging portion integrally formed with the two recesses of the goggle body with different colors, so that the entire goggle frame is more pleasing esthetically.

What is claimed is:

1. A protective goggle assembly, comprising an integrally formed goggle frame, a lens shaped corresponding to the goggle frame, and a strap having its respective ends attached to buckles; wherein:

a rigid goggle body provided on a front side of the goggle frame has an engaging portion located at a middle section of an upper side of the goggle body and including a groove opening outwards, and a concave section located at the middle section of a lower side of the goggle body and provided with a vertical through hole located adjacent to the concave section; and the lens has a connecting portion located at a middle section of an upper side and fittable into the groove of the goggle body, and a downwardly extending protrusion located at the middle section of a lower side and insertable into the vertical through hole on the goggle body;

the goggle body has a designed through hole on each of two sides thereof with raised portions protruding outwards from a periphery of the designed through hole, and a tenon located on a side of each of the designed through holes;

a designed through hole on each of two sides of the lens corresponds to the respective designed through holes on the goggle body with an aperture being located on a side of each of the designed through holes on the lens for receiving the corresponding tenon; and each of the buckles attached to the strap has an engaging section extending from a side thereof, and a boundary portion formed at an end of the engaging section for sequentially penetrating the respective designed through holes of the lens and the goggle body, so that when the two buckles are rotated, the boundary portions of the respective engaging sections press stably against an inner surface of the two designed through holes of the goggle body;

whereby the goggle frame, the lens and the strap is assembled in a simple and convenient way so as to be stably positioned and quickly disassembled when not in use.

2. The protective goggle assembly as claimed in claim 1, wherein a resilient face engaging portion located adjacent to a side of the rigid goggle body of the goggle frame includes a plurality of air vents on two sides of a lower end of the resilient face engaging portion, so that the protective goggle assembly allows good ventilation when in use.

\* \* \* \* \*